US007927855B2

(12) United States Patent
Clendennen et al.

(10) Patent No.: US 7,927,855 B2
(45) Date of Patent: *Apr. 19, 2011

(54) ESTERS OF LONG-CHAIN ALCOHOLS AND PREPARATION THEREOF

(75) Inventors: Stephanie Kay Clendennen, Kingsport, TN (US); Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 356 days.

This patent is subject to a terminal disclaimer.

(21) Appl. No.: 11/890,974

(22) Filed: Aug. 8, 2007

(65) Prior Publication Data
US 2009/0042271 A1 Feb. 12, 2009

(51) Int. Cl.
C12N 9/20 (2006.01)
C12N 9/50 (2006.01)
C07C 69/76 (2006.01)
A61F 2/00 (2006.01)
(52) U.S. Cl. .......................... 435/198; 435/219; 560/51
(58) Field of Classification Search ........................ None
See application file for complete search history.

(56) References Cited

U.S. PATENT DOCUMENTS

| 4,271,083 | A  | 6/1981  | Morimoto et al. |
| 4,407,757 | A  | 10/1983 | Morimoto et al. |
| 6,756,045 | B1 | 6/2004  | Neudecker et al. |
| 2004/0197282 | A1 | 10/2004 | Neudecker et al. |
| 2005/0175559 | A1 | 8/2005  | DiNardo et al. |
| 2005/0197407 | A1 | 9/2005  | DiNardo et al. |
| 2009/0203779 | A1 | 8/2009  | Clendennen et al. |

FOREIGN PATENT DOCUMENTS

| EP | 1 449 511 A1 | 8/2004 |
| EP | 1 702 614 A1 | 9/2006 |
| WO | WO 2005/070370 A1 | 8/2005 |
| WO | WO 2009/0202586 A2 | 2/2009 |

OTHER PUBLICATIONS

Pignatello et al. "A Calorimetric Evaluation of the Interaction of Amphiphilic Prodrugs of Idebenone with a Biomembrane Model" Journal of Colloid and Interface Science 299 (2006) 626-635.*
Schurer "Implementation of Fatty Acid Carriers to skin Irritation and the Epidermal Barrier" Contact Dermatitis 2002, 47, 199-205.*
Notification of Transmittal of the International Search Report and the Written Opinion of the International Searching Authority, or the Declaration date of mailing Jan. 26, 2009 received in International Patent Application No. PCT/US2008/009386.
Pignatello, R. et al.; "A calorimetric evaluation of the interaction of amphiphilic prodrugs of idebenone with a biomembrane model"; Journal of Colloid and Interface Science; 299; (2006); pp. 626-635.
Yu, C. A. et al.; "Syntheses of Biologically Active Ubiquinone Derivatives"; Biochemistry; 21; 1982; pp. 4096-4101.
Kojima, Hajime et al.; "Evaluation of skin irritation in a reconstituted human dermal model (3-D model) using water insoluble fatty acids, fatty alcohols and hydrocarbons"; Altern. Animal Test. Experiment; 1998; pp. 201-210; Volume-Issue No. 5.
McDaniel, D. H. et al.; "Clinical efficacy assessment in photodamaged skin of 0.5% and 1.0% idebenone"; Journal of Cosmetic Dermatology; 2005; pp. 167-173; Volume-Issue No. 4; Blackwell Publishing.
Schürer, N. Y.; "Implementation of fatty acid carriers to skin irritation and the epidermal barrier"; Contact Dermatitis; 2002; pp. 199-205; Volume-Issue No. 47; Blackwell Munksgaard; Denmark.
Notification of Transmittal of the International Search Report and the Written Opinion of the International Searching Authority, or the Declaration date of mailing Jun. 26, 2009 received in corresponding International Application No. PCT/US2009/000404.
Bartee, S.D. et al.; "Effects of antioxidants on the oxidative stability of oils containing arachidonic, docosapentaaenoic and docosahexaenoic acids"; *J Amer Oil Chem Soc*; 2007; 84: 363-68.
Demarco et al., *Biochem. Pharmacol.*; 2002; 64; 1503-1512.
Kojima, Hajime et al.; "Evaluation of skin irritation in a reconstituted human dermal model (3-D model) using water insoluble fatty acids, fatty alcohols and hydrocarbons"; Altern. Animal Test. Experiment; 1998; pp. 201-210; Volume-Issue No. 5.
McDaniel, D. H. et al.; "Clinical efficacy assessment in photodamaged skin of 0.5% and 1.0% idebenone"; Journal of Cosmetic Dermatology; 2005; pp. 167-173; Volume-Issue No. 4; Blackwell Publishing.
Narayanan, S. et al.; "Scavenging properties of metronidazole on free oxygen radicals in a skin lipid model system"; *J Pharm Pharmacol*; Aug. 2007; 59(8):1125-30.
Schürer, N. Y.; "Implementation of fatty acid carriers to skin irritation and the epidermal barrier"; Contact Dermatitis; 2002; pp. 199-205; Volume-Issue No. 47; Blackwell Munksgaard; Denmark.

\* cited by examiner

*Primary Examiner* — Robert A Wax
*Assistant Examiner* — Danah Al-Awadi
(74) *Attorney, Agent, or Firm* — Brett L Nelson; Bernard J. Graves, Jr.

(57) ABSTRACT

Disclosed are esters and a process for the preparation of the esters represented by formula 1:

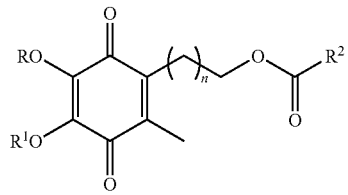

The process includes reacting an alcohol with a long-chain acid $R^2COOH$ or long-chain ester $R^2COOR^4$ in the presence of an organic solvent and an enzyme with or without the removal of water.

19 Claims, No Drawings

ESTERS OF LONG-CHAIN ALCOHOLS AND PREPARATION THEREOF

BACKGROUND OF THE INVENTION

Long-chain alcohols have a number of uses in cosmetics and personal care. Long chain alcohols such as behenyl alcohol are useful as emollients to make skin smoother and prevent moisture loss. Other alcohols are useful as active ingredients. One such example is idebenone, which is a potent anti-oxidant which has been shown to reduce skin roughness and fine lines and wrinkles, and also to improve photodamaged skin (McDaniel, D. H.; Neudecker, B. A.; Dinardo, J. C.; Lewis II, J. A.; Maibach, H. I. *Journal of Cosmetic Dermatology* 2005, 4, 167-173). This material has also been claimed to induce protective and regenerative effects (U.S. Pat. No. 6,756,045), reduce skin hyperpigmentation (US Patent Publication 2005/0175559), and to reduce irritation and/or inflammatory reaction in human skin (US Patent Application Publication 2005/0197407). Ester derivatives of idebenone may improve the physical properties of this orange solid. In addition, esters of idebenone with fatty acids will hydrolyze in the skin to afford idebenone along with the fatty acid derivative which may also have positive benefits.

The classical chemical preparation of esters such as idebenone involves either the reaction of the alcohol with an acid, acid chloride, or acid anhydride. These methods often use either harsh reagents or high temperatures, which can cause difficulties if either the alcohol or the acid derivative is unstable.

There have been reports of short-chain esters of idebenone and similar molecules. U.S. Pat. No. 4,271,083 reports alkyl esters of idebenone and similar molecules where the alkyl ester has 1-4 carbon atoms. U.S. Pat. No. 4,407,757 describes acetate esters of idebenone and similar molecules. U.S. Pat. No. 6,756,045 describes hydrophilic esters of idebenone, particularly sulfonic acid esters. None of these references prepared these materials by enzymatic means.

None of the references describe a derivative of idebenone with a long-chain fatty acid, which may be more physiologically compatible and less irritating to skin than a shorter chain fatty acid (Schurer, 2002, Contact Dermatitis 47: 199; Kojima et al., 1998, Altern Animal Test. Exper. 5: 201).

BRIEF SUMMARY OF THE INVENTION

A first embodiment according to the present invention concerns a composition, comprising an ester represented by the general formula 1:

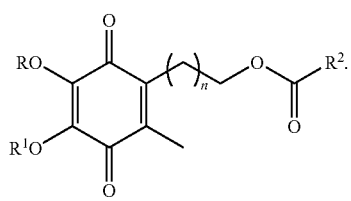

R and $R^1$ are independently a $C_1$-$C_4$ alkyl, $R^2$ is selected from the group consisting of a $C_5$-$C_{22}$ alkyl, a $C_5$-$C_{22}$ alkenyl, a $C_5$-$C_{20}$ dienyl, a $C_6$-$C_{22}$ trienyl, a $C_8$-$C_{22}$ tetraenyl and mixtures thereof, and n is 2-12.

Another embodiment of the present invention concerns a process for the preparation of an ester represented by formula 1:

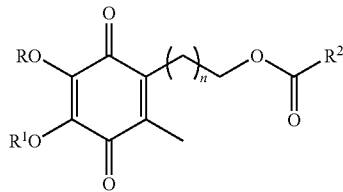

comprising reacting an alcohol represented by formula 2:

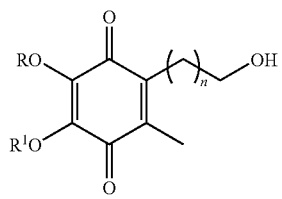

with a long-chain acid $R^2COOH$ or long-chain ester $R^2COOR^4$ in the presence of an inert solvent and an enzyme. R and $R^1$ are independently a $C_1$-$C_4$ alkyl, $R^2$ is selected from the group consisting of a $C_5$-$C_{22}$ alkyl, a $C_5$-$C_{22}$ alkenyl, a $C_5$-$C_{20}$ dienyl, a $C_6$-$C_{22}$ trienyl, a $C_8$-$C_{22}$ tetraenyl and mixtures thereof, n is 2-12, and $R^4$ is a $C_1$-$C_4$ alkane or alkene.

DETAILED DESCRIPTION

The present invention concerns a series of novel esters of long-chain alcohols represented by the general formula 1:

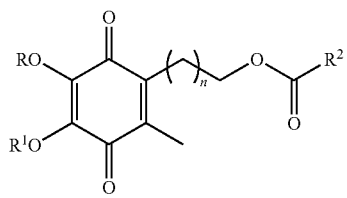

wherein
R and $R^1$ are selected from branched- and straight-chain $C_1$-$C_4$ alkyl, $R^2$ is selected from substituted and unsubstituted, branched- and straight-chain saturated $C_5$-$C_{22}$ alkyl, substituted and unsubstituted, branched- and straight-chain $C_5$-$C_{22}$ alkenyl, substituted and unsubstituted, branched- and straight-chain $C_5$-$C_{20}$ dienyl, substituted and unsubstituted, branched- and straight-chain $C_6$-$C_{22}$ trienyl, and substituted and unsubstituted, branched- and straight-chain $C_8$-$C_{22}$ tetraenyl or mixtures thereof, and n is 2-12.

The alkyl, alkenyl, dienyl, trienyl, and tetraenyl groups which may be represented by $R^2$ may be straight- or branched-chain aliphatic hydrocarbon radicals containing up to about 20 carbon atoms and may be substituted, for example, with one to three groups selected from $C_1$-$C_6$-alkoxy, cyano, $C_2$-$C_6$-alkoxycarbonyl, $C_2$-$C_6$-alkanoyloxy, hydroxy, aryl, heteroaryl, thiol, thioether, and halogen. The terms "$C_1$-$C_6$-alkoxy", "$C_2$-$C_6$-alkoxycarbonyl", and "$C_2$-$C_6$-alkanoyloxy" are used to denote radicals corresponding to the structures —$OR^3$, —$CO_2 R^3$, and —$OCOR^3$, respectively, wherein $R^3$ is $C_1$-$C_6$-alkyl or substituted $C_1$-$C_6$-alkyl.

Examples of the compounds of the invention include those represented by formula 1 wherein acyl group $R^2$—CO is linoleoyl, stearoyl, linolenoyl, conjugated linoleoyl, palmoyl, and oleoyl or mixtures thereof.

Another embodiment of the present invention concerns a process for the preparation of esters 1:

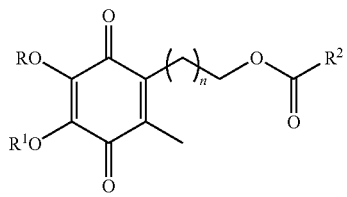

comprising the reaction of alcohol 2

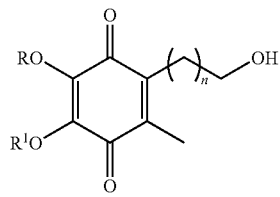

with a long-chain acid $R^2COOH$ or long-chain ester $R^2COOR^4$ in the presence of an inert solvent and an enzyme with or without methods for the removal of water wherein R, $R^1$, and $R^2$ are as defined above and $R^4$ is a straight or branched $C_1$-$C_4$ alkane or alkene. For the purposes of the present invention, a long-chain acid or a long-chain ester would include those acids or esters having chains of 5 carbon atoms or more.

The straight or branched $C_1$-$C_4$ alkyl or alkenyl group represented by $R^4$ may be chosen from methyl, ethyl, n-propyl, i-propyl, n-butyl, s-butyl, vinyl, 1-propenyl, 2-propenyl, 2-butenyl and the like.

The process is carried out in an inert solvent chosen from cyclic or acyclic ether solvents such as diethyl ether, diisopropyl ether, tert-butyl methyl ether, or tetrahydrofuran, aromatic hydrocarbons such as benzene, toluene, or xylene, aliphatic or alicyclic saturated or unsaturated hydrocarbons such as hexane, heptane, cyclohexane, or limonene, halogenated hydrocarbons such as dichloromethane, dichloroethane, dibromoethane, tetrachloroethylene, or chlorobenzene, polar aprotic solvents such as acetonitrile, dimethyl formamide, or dimethyl sulfoxide, or mixtures thereof. Examples of acceptable solvents include toluene, limonene, and acetonitrile. The process may be carried out at a temperature between about −100° C. and the boiling point of the solvent, or between about 0-60° C., or even between about 20-50° C. The amount of long-chain acid or long-chain ester may be between 0.85 and 20 equivalents based on the amount of the alcohol represented by 2, or between 1 and 10 equivalents based on the amount of alcohol. The enzyme used in the process is chosen from a protease, a lipase, or an esterase. For example, lipases may be used and may be in the form of whole cells, isolated native enzymes, or immobilized on supports. Examples of these lipases include but are not limited to Lipase PS "Amano" (from *Pseudomonas* sp), Lipase PS-C "Amano" (from *Psuedomonas* sp immobilized on ceramic), Lipase PS-D "Amano" (from *Pseudomonas* sp immobilized on diatomaceous earth), LipoPrime® 50T, Lipozyme® TL IM, or Novozym® 435 (from *Candida antarctica* immobilized on acrylic resin).

The process may optionally be carried out in the presence of various addenda chosen from molecular sieves or ion exchange resins. For example, 3A, 4A, or 5A molecular sieves can be used.

The product of the process may be isolated using methods known to those of skill in the art, e.g., extraction, filtration, or crystallization. The product 1 may be purified if necessary using methods known to those of skill in the art, e.g., extraction, chromatography, distillation, or crystallization.

EXAMPLES

This invention can be further illustrated by the following examples, although it will be understood that these examples are included merely for purposes of illustration and are not intended to limit the scope of the invention unless otherwise specifically indicated.

Example 1

Preparation of Idebenone Linoleate (1a)(EX00011-037)

Idebenone (2a, $R=R^1$=Me, n=9; 547 mg; 1.6 mmol) was dissolved in 10 mL of toluene. Linoleic acid (2.18 g; 4.9 equiv) was added followed by 641 mg of 4A molecular sieves and 309 mg of Novozym® 435. The reaction mixture was stirred at ambient temperature for 2 days, at which point tlc analysis (1:1 ethyl acetate:heptane eluant) indicated no remaining idebenone. The solids were removed by filtration and the precipitate washed with toluene. The combined filtrate and washes were concentrated at reduced pressure. The residue was dissolved in heptane (22 mL) and washed with a mixture of 11 mL of methanol and 11 mL of 10% aqueous potassium carbonate. The organic layer was further washed with a mixture of 11 mL of methanol, 4 mL of saturated sodium bicarbonate, and 7 mL of water. The organic layer was then dried with sodium sulfate and concentrated to afford 0.84 g (87%) of 1a ($R=R^1$=Me, n=9).
$^1$H NMR (CDCl3) δ5.40-5.30 (m, 4H); 4.049 (t, 2H, J=6.87 Hz); 3.988 (s, 6H); 2.768 (t, 2H, J=5.77 Hz); 2.45 (m, 2H); 2.288 (t, 2H, J=7.42 Hz); 2.08-2.01 (m, 3H); 2.009 (s, 3H); 1.64-1.57 (m, 3H); 1.40-1.29 (m, 30H); 0.89 (t, 3H, J=6.60 Hz).

Example 2

Preparation of Idebenone Conjugated Linoleate (1b)(EX00011-037)

Idebenone (2a; 499 mg; 1.48 mmol) was dissolved in 10 mL of toluene. Conjugated linoleic acid (Tonalin® FFA; 2.07 g; 5 equiv) was added followed by 500 mg of 4A molecular sieves and 300 mg of Novozym® 435. The reaction mixture was stirred at ambient temperature for 2 days, at which point tlc analysis (1:1 ethyl acetate:heptane eluant) indicated a small amount of idebenone. Additional 4A molecular sieves were added and the mixture was stirred for an additional 2 days, at which point tlc analysis indicated no remaining idebenone. The solids were removed by filtration and the precipitate washed with toluene. The combined filtrate and washes were concentrated at reduced pressure. The residue was dissolved in heptane (50 mL) and washed twice with a 1:1 mixture of methanol and 10% aqueous potassium carbonate (50 mL, then 20 mL). The organic layer was further washed with a mixture of 15 mL of methanol, 5 mL of saturated sodium bicarbonate, and 10 mL of water. The organic layer was then dried with sodium sulfate and concentrated to afford 850 mg (96%) of 1b.

$^1$H NMR (CDCl3) δ6.33-6.24 (m,1H); 5.935 (t,1H, J=11.0 Hz); 5.60-5.60 (m,1H); 5.35-5.26 (m,1H); 4.049 (t, 2H, J=6.60 Hz); 3.988 (s, 3H); 3.986 (s, 3H); 2.445 (t, 2H, J=6.87 Hz); 2.285 (t, 2H, J=7.42 Hz); 2.18-2.05 (m, 3H); 2.009 (s, 3H); 1.62-1.56 (m, 5H); 1.30-1.23 (m, 30H); 0.91-0.86 (m, 3H).

Example 3

Preparation of Idebenone Ester with Pamolyn 200 Linoleic Acid (1c) (EX00011-037)

Idebenone (2a; 501 mg; 1.48 mmol) was dissolved in 10 mL of toluene. Pamolyn 200® linoleic acid (2.07 g; 5 equiv) was added followed by 500 mg of 4A molecular sieves and 300 mg of Novozym® 435. The reaction mixture was stirred at ambient temperature for 2 days, at which point tlc analysis (1:1 ethyl acetate:heptane eluant) indicated a small amount of idebenone. Additional 4A molecular sieves were added but no change was observed by tlc. The solids were removed by filtration and the precipitate washed with toluene. The combined filtrate and washes were concentrated at reduced pressure. The residue was dissolved in heptane (50 mL) and washed with a 1:1 mixture of methanol and 10% aqueous potassium carbonate (50 mL). The organic layer was further washed with a mixture of 15 mL of methanol, 5 mL of saturated sodium bicarbonate, and 10 mL of water. The organic layer was then dried with sodium sulfate and concentrated to afford 798 mg (90%) of 1b.

Example 4

Preparation of Idebenone octanoate (1d)(EX00011-037)

Idebenone (2a; 500 mg; 1.48 mmol) was dissolved in 10 mL of toluene. Octanoic acid (1.07 g; 5 equiv) was added followed by 500 mg of 4A molecular sieves and 300 mg of Novozym® 435. The reaction mixture was stirred at ambient temperature for 2 days, at which point tlc analysis (1:1 ethyl acetate:heptane eluant) indicated no idebenone. The solids were removed by filtration and the precipitate washed with toluene. The combined filtrate and washes were concentrated at reduced pressure. Concentration in vacuo afforded 630 mg (92%) of 1d.

$^1$H NMR (CDCl3) δ4.051 (t, 2H, J=6.87 Hz); 3.990 (s, 3H); 3.987 (s, 3H); 2.446 (t, 2H, J=7.15 Hz); 2.289 (t, 2H, J=7.42 Hz); 2.010 (s, 3H); 1.61-1.57 (m, 5H); 1.33-1.28 (m, 30H); 0.878 (t, 3H, J=6.60 Hz).

The invention has been described in detail with particular reference to preferred embodiments thereof, but it will be understood that variations and modifications can be effected within the spirit and scope of the invention.

We claim:

1. A composition, comprising an ester represented by the general formula 1:

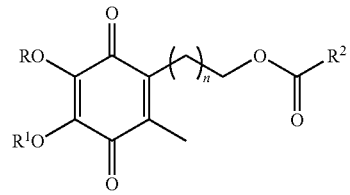

wherein
R and $R^1$ are independently a $C_1$-$C_4$ alkyl,
$R^2$ is selected from the group consisting of a $C_{11}$-$C_{22}$ alkyl, a $C_5$-$C_{22}$ alkenyl, a $C_5$-$C_{20}$ dienyl, a $C_6$-$C_{22}$ trienyl, a $C_8$-$C_{22}$ tetraenyl and mixtures thereof, and
n is 2-12.

2. The composition according to claim 1, wherein the alkyl, alkenyl, dienyl, trienyl, and tetraenyl group of $R^2$ is an aliphatic hydrocarbon radical containing up to about 22 carbon atoms.

3. The composition according to claim 2, wherein the aliphatic hydrocarbon containing up to 22 carbon atoms is substituted with one to three groups selected from the group consisting of $C_1$-$C_6$-alkoxy, cyano, $C_2$-$C_6$-alkoxycarbonyl, $C_2$-$C_6$-alkanoyloxy, hydroxy, aryl, heteroaryl, thiol, thioether, and halogen.

4. The composition according to claim 1 wherein an acyl group $R^2$—CO is selected from the group consisting of linoleoyl, stearoyl, linolenoyl, conjugated linoleoyl, palmoyl, oleoyl and mixtures thereof.

5. A process for the preparation of an ester represented by formula 1:

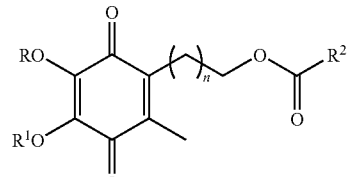

comprising reacting an alcohol represented by formula 2

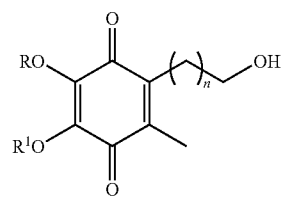

with a long-chain acid $R^2$COOH or long-chain ester $R^2$COO$R^4$ in the presence of an inert solvent and an enzyme,
wherein R and $R^1$ are independently a $C_1$-$C_4$ alkyl,
$R^2$ is selected from the group consisting of a $C_{11}$-$C_{22}$ alkyl, a $C_5$-$C_{22}$ alkenyl, a $C_5$-$C_{20}$ dienyl, a $C_6$-$C_{22}$ trienyl, a $C_8$-$C_{22}$ tetraenyl and mixtures thereof,
n is 2-12, and
$R^4$ is a $C_1$-$C_4$ alkane or alkene.

6. The process according to claim 5, wherein a long-chain acid $R^2$COOH is used and water is removed during the process.

7. The process according to claim 5, wherein the $C_1$-$C_4$ alkyl or alkenyl group represented by $R^4$ is selected from the group consisting of methyl, ethyl, n-propyl, i-propyl, n-butyl, s-butyl, vinyl, 1-propenyl, 2-propenyl, and 2-butenyl.

8. The process according to claim 5, wherein the solvent is selected from the group consisting of an ether solvent, an aromatic hydrocarbon solvent, an aliphatic hydrocarbon solvent, an alicyclic hydrocarbon solvent, a halogenated hydrocarbon solvent, a polar aprotic solvent, and mixtures thereof.

9. The process according to claim 8, wherein the solvent is toluene, limonene, acetonitrile, or mixtures thereof.

10. The process according to claim 5, wherein the process is reacted at a temperature of between about −100° C. and a boiling point of the solvent.

11. The process according to claim 10, wherein the process is reacted at a temperature of between about 0-60° C.

12. The process according to claim 11, wherein the process is reacted at a temperature of between about 20-50° C.

13. The process according to claim 5, wherein the long-chain acid or long-chain ester is present in an amount of between 0.85 and 20 equivalents based on the alcohol.

14. The process according to claim 13, wherein long-chain acid or long-chain ester is present in an amount of between 1 and 10 equivalents.

15. The process according to claim 5, wherein the enzyme used is selected from the group consisting of a protease, a lipase, and an esterase.

16. The process according to claim 15, wherein the lipase is in the form of whole cells, isolated native enzymes, or immobilized on supports.

17. The process according to claim 15, wherein the lipase is selected from the group consisting of Lipase PS, Lipase PS-C, Lipase PS-D, Lipoprime 50T, Lipozyme TL IM, and Novozyme 435.

18. The process according to claim 5, wherein the ester is isolated via extraction, filtration, or crystallization.

19. The process according to claim 18, wherein the ester is purified via extraction, chromatography, distillation, or crystallization.

* * * * *